United States Patent [19]

Kaplan et al.

[11] Patent Number: 4,523,591
[45] Date of Patent: Jun. 18, 1985

[54] POLYMERS FOR INJECTION MOLDING OF ABSORBABLE SURGICAL DEVICES

[76] Inventors: Donald S. Kaplan, 7 White Oak La., Weston, Conn. 06883; Ross R. Muth, 97 Clearview Dr., R.D. 2, Conn. 06804

[21] Appl. No.: 436,056

[22] Filed: Oct. 22, 1982

[51] Int. Cl.$^3$ .................... A61L 15/04; A61L 17/00
[52] U.S. Cl. ............................. 128/334 R; 128/335.5
[58] Field of Search ............. 128/334 R, 334 C, 335, 128/335.5, 325, 92 BB; 528/357

[56] References Cited

U.S. PATENT DOCUMENTS

| | | | |
|---|---|---|---|
| 2,668,162 | 2/1954 | Lowe | 528/357 |
| 2,703,316 | 3/1955 | Schneider | 528/357 |
| 2,758,987 | 8/1956 | Salzberg | 528/357 |
| 3,225,766 | 12/1965 | Baptist et al. | 128/335.5 |
| 3,297,033 | 1/1967 | Schmitt et al. | 128/335.5 |
| 3,422,181 | 1/1969 | Chirgwin, Jr. | 264/345 |
| 3,463,158 | 8/1969 | Schmitt et al. | 128/334 |
| 3,531,561 | 9/1970 | Trehn | 264/210 |
| 3,565,869 | 2/1971 | DeProspero | 528/357 |
| 3,597,449 | 8/1971 | DeProspero et al. | 260/340.2 |
| 3,620,218 | 11/1971 | Schmitt et al. | 128/334 |
| 3,626,948 | 12/1971 | Glick et al. | 128/335.5 |
| 3,636,956 | 1/1972 | Schneider | 128/335.5 |
| 3,736,646 | 6/1973 | Schmitt et al. | 29/458 |
| 3,772,420 | 11/1973 | Glick et al. | |
| 3,773,919 | 11/1973 | Boswell et al. | 424/19 |
| 3,792,010 | 2/1974 | Wasserman et al. | 528/357 |
| 3,797,499 | 3/1974 | Schneider | 128/334 R |
| 3,839,297 | 10/1974 | Wasserman et al. | 528/357 |
| 3,867,190 | 2/1975 | Schmitt et al. | 117/138.8 |
| 3,875,937 | 4/1975 | Schmitt et al. | 128/156 |
| 3,878,284 | 4/1975 | Schmitt et al. | 264/184 |
| 3,982,543 | 9/1976 | Schmitt et al. | 128/335.5 |
| 4,060,089 | 11/1977 | Noiles | 128/335 |
| 4,137,921 | 2/1979 | Okuzumi et al. | 128/335.5 |
| 4,141,738 | 2/1979 | Rapp | 106/39 |
| 4,157,437 | 6/1979 | Okuzumi et al. | 528/354 |
| 4,175,988 | 11/1979 | Rapp | 148/189 |
| 4,243,775 | 1/1981 | Rosensaft et al. | 525/415 |
| 4,259,410 | 3/1981 | Dittmann et al. | 428/461 |
| 4,273,920 | 6/1981 | Nevin | 528/361 |
| 4,275,813 | 6/1981 | Noiles | 206/339 |
| 4,300,565 | 11/1981 | Rosensaft et al. | 128/335.5 |
| 4,302,551 | 11/1981 | Horn et al. | 521/163 |
| 4,387,769 | 6/1983 | Erbstoesser et al. | 166/295 |

OTHER PUBLICATIONS

*Biocompatibility of Clinical Implant Materials,* D. F. Williams (Ed.), vol. II, chapter 9 (1981).
"Biodegradable Polymers for Use in Surgery—Polyglycolic/Poly(Actic Acid) Homo-and Copolymers:1," D. K. Gilding and A. M. Reed, *Polymer,* 1979, vol. 20, Dec., pp. 1459–1464.

Primary Examiner—Richard J. Apley
Assistant Examiner—Gregory Beaurage
Attorney, Agent, or Firm—John E. Nathan; Richard M. Barnes

[57] ABSTRACT

Absorbable, substantially amorphous surgical fasteners having good in vivo strength-retaining and absorption characteristics may be made of copolymers of lactide and glycolide made from 70–85% m lactide and 15–30% m glycolide provided the inherent viscosity and glass transition temperature of the copolymers have at least certain minimum values.

24 Claims, No Drawings

POLYMERS FOR INJECTION MOLDING OF ABSORBABLE SURGICAL DEVICES

BACKGROUND OF THE INVENTION

Polymers and copolymers of, and absorbable surgical devices made from, lactide and/or glycolide and releated compounds are well-known. See, e.g., U.S. Pat. Nos. 2,668,162, 2,703,316, 2,758,987, 3,225,766, 3,297,033, 3,422,181, 3,531,561, 3,565,869, 3,620,218, 3,626,948, 3,636,956, 3,736,646, 3,772,420, 3,773,919, 3,792,010, 3,797,499, 3,839,297, 3,867,190, 3,878,284, 3,982,543, 4,060,089, 4,137,921, 4,157,437, 4,243,775, 4,273,920, and 4,300,565, U.K. Pat. No. 779,291, D. K. Gilding et al., "Biodegradable polymers for use in surgery—polyglycolic/poly(lactic acid) homo- and copolymers: 1, "*Polymer,* Volume 20 pages 1459-1464 (1979), and D. F. Williams (ed.), *Biocompatibility of Clinical Implant Materials,* Vol. II, ch. 9: "Biodegradable Polymers" (1981).

Some of those documents disclose purifying the polymer(s) or copolymer(s) by drying and/or removing unreacted monomer(s). See, e.g., U.S. Pat. Nos. 3,225,766, 3,422,181, 3,565,869, 3,626,948, 3,636,956, 3,772,420, 3,773,919, 4,273,920, and 4,300,565, U.K. Pat. No. 779,291, and Gilding et al. Some of those documents disclose copolymers of lactide and glycolide containing fifteen or more mole percent glycolide. See, e.g., U.S. Pat. Nos. 2,668,162, 2,703,316, 3,297,033, 3,620,218, 3,636,956, 3,736,646, 3,773,919, 3,797,499, 3,839,297, 3,867,190, 3,982,543, and 4,273,920, Gilding et al., and Williams.

Current publicly available information indicates that those skilled in the art believe lactide/glycolide copolymers used for making surgical fasteners should be crystalline, for example, so that such fasteners can retain their strength in vivo for a sufficient amount of time. See, e.g., U.S. Pat. Nos. 2,758,987, column 1, lines 47—51; 3,636,956, column 4, lines 2-12; and Gilding, page 1463.

SUMMARY OF THE INVENTION

It has now been discovered that surgical fasteners (e.g., surgical clips and staples) that retain their strength in vivo for a sufficient amount of time and are absorbed in the body quickly enough can be made of a lactide/glycolide copolymer having no more than 20% crystallinity, provided the copolymer has certain other characteristics.

Broadly, the copolymer of this invention is a copolymer made from 70-85% m lactide and 15-30% m glycolide useful for making surgical fasteners, said copolymer having a glass transition temperature of at least 56° C. when measured by differential scanning calorimetry at 20° C./min, an inherent viscosity of at least 1.3 when measured in chloroform at 30° C. at a concentration of 0.25 g/dl, and no more than 20% crystallinity.

In another aspect, the invention relates to a substantially amorphous fastener, which fastener comprises a copolymer made from 70-85% m lactide and 15-30% m glycolide and having a glass transition temperature of at least 54° C. when measured by differential scanning calorimetry at 20° C./min and an inherent viscosity of at least 0.9 when measured in chloroform at 30° C. at a concentration of 0.25 g/dl.

In yet another aspect, the invention relates to a method of making the fastener from the copolymer, which method comprises (a) copolymerizing the lactide and glycolide; (b) purifying the resulting crude product by removing unreacted monomers sufficiently to raise the glass transition temperature to at least 56° C. when measured by differential scanning calorimetry at 20° C./min and maintaining the inherent viscosity at at least 1.3 when measured in chloroform at 30° C. at 0.25 g/dl; (c) drying the copolymer until it is sufficiently dry; and (d) forming the fastener from the purified dry copolymer.

It is most surprising that, contrary to the teachings of the prior art, a substantially amorphous absorbable fastener made of lactide/glycolide copolymer can be made to have the desired absorption and strength-retaining properties.

DETAILED DESCRIPTION OF THE INVENTION

Specifically, the copolymer of this invention is made from at least 15% (mole percent) but no more than 30% m glycolide so that the fastener made from it is not too brittle and does not absorb too slowly or too quickly and is not more than 20% crystalline (compare FIG. 6a of) Gilding). Preferably, the fastener is substantially amorphous. As used herein, "substantially amorphous" means having 10% or less crystallinity (see, e.g., U.S. Pat. No. 3,878,284, column 3, lines 16-18). The copolymer usually should not be more than 20% crystalline so that the fastener will not be more than 10% crystalline. Crystallinity decreases with fastener forming processes that heat the copolymer above melting and then cool rapidly enough to prevent reorientation (e.g., the preferred injection molding process). With those processes, the copolymer itself can be of relatively high crystallinity. With fastener forming processes in which crystallinity is not decreased appreciably during forming, the copolymer must itself be of low crystallinity for the fastener to be substantially amorphous.

The copolymer before being formed into the fastener should have an inherent viscosity of at least 1.3 when measured in chloroform at 30° C. in a concentration of 0.25 g/dl (grams of copolymer per deciliter of solution). Use of a Ubbelohde Viscometer is preferred. The fastener itself should have an inherent viscosity of at least 0.9, which corresponds to an average molecular weight of about 90,000. (The process of forming the fastener from the copolymer tends to reduce the inherent viscosity.)

The glass transition temperature when measured by differential scanning calorimetry at 20° C./min should be at least 56° C. for the copolymer before being formed into the fastener and at least 54° C. and preferably at least 56° C. after forming.* (The fastener forming process tends to reduce the glass transition temperature also.)

* A Perkin-Elmer Model DSC-2 Differential Scanning Calorimeter is used. Seven to eight mg of the sample are sealed in an aluminum sample pan, which is then placed in the measuring head of the calorimeter. The sample is heated to relieve all stress and orientation, which may cause spurious thermal effects (e.g., heated at a rate of 20° C./min to a temperature of 170°-180° C.) and then cooled at 10° C./min to a temperature below the expected glass transition temperature (typically to 0° C.). The sample is scanned at a heating rate of 20° C./min through the glass transition. The glass transition temperature is taken as the mid-point of the transition region. See Collins et al., *Experiments In Polymer Science,* pages 432-433 (1973).

The surgical fasteners of this invention will retain their in vivo strength for varying amounts of time, depending on the particular fastener construction (e.g., staple or clip) and on the characteristics of the particular copolymer used. Desirably, staples within this invention will retain adequate strength in vivo for at least about two to three weeks and clips of this invention will retain their in vivo strength for at least about one week. Usually, at least 95% of a surgical fastener of this invention will be absorbed into the body within six to eight months of implantation. In certain instances, it may be desirable to use fasteners that are absorbed more slowly.

The copolymers of this invention are made by copolymerizing lactide and glycolide in any suitable manner known to those skilled in the art. See, e.g., the documents cited in "Background of the Invention." A preferred procedure for making these copolymers is as follows.

Hydroxyacetic acid (glycolic acid) is heated under nitrogen to 180° C. to remove water. Pressure is then reduced and heating is continued for two hours to yield a prepolymer of polyglycolic acid, which is recovered and powdered.

The prepolymer is heated in the presence of $Sb_2O_3$ at 275° C. under low pressure with an Argon purge and stirring. The prepolymer cracks and glycolide is distilled over and recovered in a cold vacuum receiver. Any purification technique that yield pure enough monomers may be used. As will be understood by one skilled in the art, the monomers must be of sufficient purity so that the copolymer has at least the minimum inherent viscosity. Preferably, the glycolide is purified by conventional techniques, such as distillation, crystallization, and sublimation.

L-lactide is used alone or in combination with a small amount of the DL racemer. L-lactide is purified by crystallization from toluene solution. The DL racemer, if used, is purified by crystallization from ethyl acetate.

As to the polymerization itself, a mixture of the purified glycolide and lactide is charged to a reactor under an Argon blanket. A solution of stannous octoate catalyst in diethyl ether is added to give 0.02% w of catalyst, based on the total weight of glycolide and lactide. The reactor is further purged with Argon and held at 5 psi while heating to 170°–175° C. Pressure and temperature are maintained for six hours.

The reaction product is isolated, comminuted, and treated (as will be described below) to remove residual reactants. Polymer particle size is usually a few millimeters. Particles too small are undesirable. A sufficient amount of unreacted monomer is removed so that the resulting polymeric product has at least the desired minimum glass transition temperature and inherent viscosity, as measured in the manners specified above.

Any method capable of removing the unreacted monomers from the crude reaction product may be used, provided that method results in the copolymer having at least the desired minimum glass transition temperature and inherent viscosity and does not adversely affect any other important properties of the copolymer, e.g., reprecipitation may be used. The preferred purification procedure is as follows.

After comminution, the crude reaction product is contacted with ethyl ether for about 72 hours in a Soxhlet-type extractor to remove unreacted monomer. Typically, 4–10% of the starting monomers remain unreacted, and the glass transition temperature of the crude copolymer is approximately 50° C. Removal of unreacted monomers raises the glass transition temperature. As will be understood by one skilled in the art, the composition of the copolymer may differ slightly from the composition of the starting monomeric mixture because the lactide and glycolide are not of equal reactivity.

After the extraction period, the partially purified copolymer is slowly heated under vacuum from ambient temperature to 140° C. over a period of about 48 hours. The slow rate of heating is important to prevent melting (strictly speaking, flowing together) of the copolymer particles and to remove any water present. Desirably, dry inert gas is used to purge the system, and occasionally the heating step may require more than 48 hours to reach the desired glass transition temperature. The combination of slow heating and purging with dry gas removes any residual solvent (ethyl ether) present, thereby raising the glass transition temperature.

After removal of unreacted monomers (and of solvent, if solvent extraction is used), the purified copolymer must be dried if it was not dried enough in the monomer removal step and, in any event, stored to keep it dry. The copolymer must be as dry as possible before fastener forming because the presence of too much water in the copolymer results in the glass transition temperature and/or inherent viscosity dropping below the minimum acceptable levels during fastener forming. Generally, it is desired that the copolymer be dried to a bone dry state and stored at a relative humidity of no more than a few percent. Preferably, the purified dried copolymer is stored under a vacuum and/or with a dry inert gas pad. As will be understood by one skilled in the art, the length of storage affects the allowable relative humidity for storage, higher humidity levels being more acceptable if storage is to be for a shorter period of time.

After monomer and water removal, the absorbable fasteners are made preferably by injection molding the purified copolymer using, for example, a screw injection molding machine. The resulting fasteners contain approximately 70–85% lactide moieties and approximately 15–30% m glycolide moieties and have a glass transition temperature of at least 54° C. and preferably at least 56° C. when measured by differential scanning calorimetry at 20° C./min and an inherent viscosity of at least 0.9 when measured in chloroform at 30° C. at 0.25 g/dl.

A preheated vacuum hopper retrofitted to the screw injection molding machine has been found to be useful for maintaining the purified dried copolymer in a bone dry condition. The vacuum hopper comprises a vessel upstream of the machine's standard hopper. The vessel must be capable of operating under vacuum and of being heated.

The preferred procedure for injection molding the fasteners is to place the purified dried copolymer particles in the vacuum hopper under a vacuum, heat the hopper to 75° C., and hold temperature and vacuum for at least an hour. The pressure in the vacuum hopper is desirably no higher than 5 mm Hg and preferably no higher than 0.1 mm Hg. The stantard hopper must also be heated and dried before allowing the purified dried copolymer to pass from the vacuum hopper into the standard hopper. The entire injection molding system desirably is padded and/or purged with a dry inert gas, such as Argon.

The design of the fasteners is not critical insofar as the present invention is concerned. The fasteners may, for instance, be staples or clips. Examples of staples and clips which can be made from the copolymers of this invention are shown in U.S. Pat. No. 4,060,089 and U.S. Pat. Appln. Ser. No. 310,065, filed Oct. 9, 1981, and No.

310,412, filed Oct. 9, 1981, and two applications of David T. Green entitled "Surgical Clip Applying Methods And Apparatus, And Clips And Clip Train For Use Therein" and "Surgical Clip Applying Apparatus Having Fixed Jaws," both filed on Sept. 30, 1982. Other possible fastener designs will be known to those skilled in the art.

The advantages of this invention are shown by the absorption and strength-retaining characteristics of a series of surgical staples having essentially the constructions shown in U.S. Pat. No. 4,060,089 and U.S. Pat. Appln. Ser. Nos. 310,065 and 310,412, both filed on Oct. 9, 1981. The staples were made in the manner described above except that for some of the copolymers, removal of unreacted monomer was accomplished using methylene chloride solvent, with evaporation and drying in a vacuum oven.

The properties of the staples, glass transition temperature, inherent viscosity, and crystallinity, were determined as described above and are reported in Table I. The staples were implanted in the lumbar muscle tissue of rats, the rats sacrificed at intervals, and the absorption and tensile characteristics determined (reported in Tables II-VI).

TABLE I

| Monomer Feed Composition (Glycolide % m/Lactide % m) | Initial* Glass Transition Temperature (°C.) | Initial* Inherent Viscosity | Initial* Crystallinity (%) |
|---|---|---|---|
| 35/65 | 52 (average) | 0.63 | none detected |
| 30/70 | 53 | 1.0 (average) | none detected |
| 25/75 | 55 | 0.9 | none detected |
| 20/80 | 58 | 2.2 | trace** |
| 10/90 | *** | 0.444**** | *** |

*"Initial" means before implantation.
**By X-ray crystallography; "trace" means only a few percent, at most.
***Not determined (see Table VI).
****In dioxane; in chloroform would be even lower.

TABLE II

Absorption And Tensile For 35/65 Glycolide/Lactide

| Time After Implantation (Weeks) | Absorption (% of Initial Weight Remaining) | Tensile (% of Initial Strength Retained) |
|---|---|---|
| 1 | 99 | 115 |
| 2 | 97 | 28 |
| 3 | 91 | 8 |
| 4 | 82 | 5 |
| 5 | 70 | — |
| 6 | 59 | — |
| 7 | 43 | — |
| 8 | 26 | — |
| 9 | 26 | — |
| 10 | 21 | — |
| 11 | 17 | — |
| 12 | 18 | — |
| 13 | 10 | — |
| 14 | 8 | — |
| 15 | 6 | — |
| 16 | 5 | — |
| 17 | 3 | — |
| 18 | 2 | — |
| 19 | 2 | — |
| 20 | <2 | — |

TABLE III

Absorption And Tensile For 30/70 Glycolide/Lactide

| Time After Implantation (Weeks) | Absorption (% of Initial Weight Remaining) | Tensile (% of Initial Strength Retained) |
|---|---|---|
| 1 | 99+ | 77 |
| 2 | 99+ | 56 |
| 3 | 99+ | 32 |
| 4 | 99 | 8 |
| 5 | 94 | 13 |
| 6 | 88 | 4 |
| 7 | 75 | — |
| 8 | 62 | — |
| 9 | 50 | — |
| 10 | 37 | — |
| 11 | 31 | — |
| 12 | 25 | — |
| 13 | 22 | — |
| 14 | 18 | — |
| 15 | 17 | — |
| 16 | 14 | — |
| 17 | 10 | — |
| 18 | 8 | — |
| 19 | 6 | — |
| 20 | 5 | — |
| 21 | 4 | — |
| 22 | 3 | — |
| 23 | 2 | — |
| 24 | 2 | — |

TABLE IV

Absorption And Tensile For 25/75 Glycolide/Lactide

| Time After Implantation (Weeks) | Absorption (% of Initial Weight Remaining) | Tensile (% of Initial Strength Retained) |
|---|---|---|
| 1 | 99+ | 99 |
| 2 | 99+ | 92 |
| 3 | 99+ | 28 |
| 4 | 99+ | — |
| 5 | 99 | — |
| 6 | 98 | — |
| 7 | 95 | — |
| 8 | 92 | — |
| 9 | 89 | — |
| 10 | 85 | — |
| 11 | 80 | — |
| 12 | 77 | — |
| 13 | 68 | — |
| 14 | 62* | — |
| 15 | 54 | — |
| 16 | 47 | — |
| 17 | 43 | — |
| 18 | 39 | — |
| 19 | 32 | — |
| 20 | 28 | — |
| 21 | 24 | — |
| 22 | 21 | — |
| 23 | 18 | — |
| 24 | 16 | — |

TABLE V

Absorption And Tensile For 20/80 Glycolide/Lactide

| Time After Implantation (Weeks) | Absorption (% of Initial Weight Remaining)* | Tensile (% of Initial Strength Retained) |
|---|---|---|
| 1 | — | >100 |
| 2 | — | >100 |
| 3 | — | >100 |
| 4 | — | >100 |
| 5 | — | >100 |
| 6 | — | >100 |
| 7 | — | >100 |

TABLE V-continued

Absorption And Tensile For 20/80 Glycolide/Lactide

| Time After Implantation (Weeks) | Absorption (% of Initial Weight Remaining)* | Tensile (% of Initial Strength Retained) |
| --- | --- | --- |
| 8 | — | >100 |

*Not measured but inferentially, absorption would be minimal during the eight weeks because there was essentially no loss in tensile strength.

TABLE VI

Absorption For 10/90 Glycolide/Lactide*

| Time After Implantation (Weeks)** | Absorption (% of Initial Weight Remaining) |
| --- | --- |
| 1 | 103 |
| 2 | 102 |
| 3 | 102 |
| 4 | 102 |
| 6 | 104 |
| 9 | 112 |
| 13 | 110 |
| 17 | 94 |
| 21 | 89 |
| 26 | 80 |
| 30 | 61 |
| 34 | 63 |
| 39 | 34 |
| 43 | 38 |
| 47 | 17 |
| 51 | 17 |

*Tensile strength retention not measured for this material.
**Rounded to nearest week.

The results show that fasteners of copolymers made from 35/65 and 10/90 glycolide/lactide having glass transition temperatures and inherent viscosities that are too low are undesirable because they lose tensile strength too quickly (Table II) or they are absorbed too slowly (Table VI).

The results show that fasteners of copolymers made from 25/75 and 20/80 glycolide/lactide having glass transition temperatures and inherent viscosities that are at least the specified minimums have good absorption and tensile characteristics (Tables IV and V).

The results for the 30/70 fastener appear to be satisfactory (Table III); however, the clinical investigator reported the staples showed shrinkage, which is not desirable. Table I shows that material meets the minimum inherent viscosity but has a slightly too low glass transition temperature. The staples tested must be regarded as marginally acceptable. A fastener of a copolymer made from 30/70 glycolide/lactide whose glass transition temperature at least met the minimum would be more acceptable.

These results evidence that substantially amorphous surgical fasteners which retain a subsantial fraction of their initial tensile strength for a sufficient period after implantation yet are almost completely absorbed within 6–8 months can be made of copolymers of lactide and glycolide, provided the copolymers are of suitable composition and have the requisite inherent viscosity and glass transition temperature.

Variations and modifications will be apparent to those skilled in the art and the claims are intended to cover all variations and modifications that fall within the true spirit and scope of this invention.

We claim:

1. A method for making an absorbable surgical fastener of a copolymer made from 70–85% m lactide and 15–30% glycolide, said fastener retaining its strength in vivo for a sufficient amount of time and having a crystallinity of not more than about 5%, said method comprising the steps:
   (a) copolymerizing lactide and glycolide;
   (b) purifying the resulting crude product by removing the unreacted monomers sufficiently to raise the glass transition temperature to at least 56° C. when measured by differential scanning calorimetry at 20° C./min and maintaining the inherent viscosity at at least 1.3 when measured in chloroform at 30° C. at a concentration of 0.25 g/dl;
   (c) drying the copolymer;
   (d) forming the fastener from the purified dry copolymer; and
   (e) maintaining the crystallinity of the fastener at not more than about 5%.

2. The method of claim 1 wherein the fastener is a surgical clip.

3. The method of claim 1 wherein the fastener is a surgical staple.

4. The method of claim 1 wherein step (b) comprises extracting the unreacted monomers with a solvent.

5. The method of claim 1 wherein step (b) comprises extracting the unreacted monomers with ethyl ether and removing residual solvent from the relatively monomerfree copolymer.

6. The method of claim 5 wherein the fastener is a surgical clip.

7. The method of claim 5 wherein the fastener is a surgical staple.

8. The method of claim 1 wherein step (d) is carried out in the presence of dry inert gas.

9. The method of claim 8 wherein the fastener is a surgical clip.

10. The method of claim 8 wherein the fastener is a surgical staple.

11. The method of claim 1 wherein step (d) is carried out by injection molding.

12. The method of claim 11 wherein the fastener is a surgical clip.

13. The method of claim 11 wherein the fastener is a surgical staple.

14. An absorbable surgical fastener that retains in vivo strength for a sufficient period of time comprising a copolymer made from 70–85% m lactide and 15–30% m glycolide, said fastener having a glass transition temperature of at least 54° C. when measured by differential scanning calorimetry at 20° C./min, an inherent viscosity of at least 0.9 when measured in chloroform at 30° C. at a concentration of 0.25 g/dl, and a crystallinity of not more than 5%.

15. The surgical fastener of claim 14 wherein the fastener is a surgical clip.

16. The surgical fastener of claim 14 wherein the fastener is a surgical staple.

17. The surgical fastener of claim 14 wherein the crystallinity is not more than 1.5%.

18. The surgical fastener of claim 17 wherein the fastener is a surgical clip.

19. The surgical fastener of claim 17 wherein the fastener is a surgical staple.

20. The surgical fastener of claim 14 wherein the glass transition temperature is at least 56° C.

21. The surgical fastener of claim 20 wherein the crystallinity is not more than 1.5%.

22. The surgical fastener of claim 21 wherein the fastener is a surgical clip.

23. The surgical fastener of claim 21 wherein the fastener is a surgical staple.

24. The surgical fastener of claim 14 wherein the copolymer is made from 75–80% m lactide and 20–25% m glycolide.

* * * * *

UNITED STATES PATENT AND TRADEMARK OFFICE
CERTIFICATE OF CORRECTION

PATENT NO. : 4,523,591
DATED : June 18, 1985
INVENTOR(S) : Kaplan et al.

It is certified that error appears in the above-identified patent and that said Letters Patent is hereby corrected as shown below:

ON COVER PAGE

Under Inventors: insert --John Joseph Kennedy, 17 Abner Court, Bridgeport, Conn. 06606--

Col. 1, lines 7-8, "releated" should be --related--

Col. 4, line 57, "stantard" should be --standard--

Signed and Sealed this

Twenty-ninth Day of October 1985

[SEAL]

Attest:

Attesting Officer

DONALD J. QUIGG

Commissioner of Patents and Trademarks—Designate